(12) United States Patent
Macoviak et al.

(10) Patent No.: US 9,610,161 B2
(45) Date of Patent: Apr. 4, 2017

(54) DEVICES, SYSTEMS, AND METHODS FOR SUPPLEMENTING, REPAIRING OR REPLACING A NATIVE HEART VALVE LEAFLET

(75) Inventors: John A. Macoviak, La Jolla, CA (US); Robert T. Chang, Belmont, CA (US); David A. Rahdert, San Francisco, CA (US); Timothy R. Machold, Moss Beach, CA (US); Rick A. Soss, Burlingame, CA (US)

(73) Assignee: MVRX, INC., San Mateo, CA (US)

( * ) Notice: Subject to any disclaimer, the term of this patent is extended or adjusted under 35 U.S.C. 154(b) by 0 days.

(21) Appl. No.: 13/227,630

(22) Filed: Sep. 8, 2011

(65) Prior Publication Data

US 2011/0319990 A1 Dec. 29, 2011

Related U.S. Application Data

(62) Division of application No. 11/981,025, filed on Oct. 31, 2007, now Pat. No. 8,016,882, which is a division of application No. 10/676,815, filed on Oct. 1, 2003, now Pat. No. 7,381,220.

(51) Int. Cl.
*A61F 2/24* (2006.01)

(52) U.S. Cl.
CPC .......... *A61F 2/2445* (2013.01); *A61F 2/2454* (2013.01); *A61F 2/2418* (2013.01)

(58) Field of Classification Search
CPC ........ A61F 2/24; A61F 2/2445; A61F 2/2454; A61F 2/2418; A61F 2/2436; A61F 2/2442; A61F 2/2448; A61F 2/2463; A61F 2/2469; A61F 2/2475; A61F 2/2478

USPC .................... 623/1.24, 1.26, 2.12, 2.14, 2.18
See application file for complete search history.

(56) References Cited

U.S. PATENT DOCUMENTS

| | | | |
|---|---|---|---|
| 4,056,854 A | 11/1977 | Boretos et al. | |
| 4,275,469 A | 6/1981 | Gabbay | |
| 4,994,069 A | 2/1991 | Ritchart et al. | |
| 4,994,077 A * | 2/1991 | Dobben | A61F 2/2406 137/521 |
| 5,358,518 A * | 10/1994 | Camilli | A61F 2/2403 137/521 |
| 5,360,444 A | 11/1994 | Kusuhara | |
| 5,370,685 A | 12/1994 | Stevens | |

(Continued)

OTHER PUBLICATIONS

Templeton III et al. "Experimental Reconstruction of Cardiac Valves by Venous Pericardial Grafts", Annals of Surgery vol. 129 No. 2, Feb. 1949 pp. 161-176.

(Continued)

*Primary Examiner* — Alvin Stewart
(74) *Attorney, Agent, or Firm* — Kilpatrick, Townsend and Stockton, LLP

(57) ABSTRACT

An implant for supplementing, repairing, or replacing a native heart valve leaflet or leaflets provides a scaffold, which defines a pseudo-annulus. The implant further has at least two struts in generally oppositely spaced apart positions on the scaffold. The scaffold can be placed in an elastically loaded condition in a heart with the struts engaging tissue at or near the leaflet commissures of a heart valve annulus, to reshape the annulus for leaflet coaptation. The implant further provides a neoleaflet element coupled to the scaffold within pseudo-annulus, to provide a one-way valve function.

3 Claims, 9 Drawing Sheets

(56) References Cited

U.S. PATENT DOCUMENTS

| | | | | |
|---|---|---|---|---|
| 5,545,241 | A | 8/1996 | Vanderauwera et al. | |
| 5,607,465 | A * | 3/1997 | Camilli | A61F 2/2418 604/104 |
| 5,716,397 | A | 2/1998 | Myers | |
| 5,776,189 | A | 7/1998 | Khalid | |
| 5,792,155 | A | 8/1998 | Van Cleef | |
| 5,824,061 | A * | 10/1998 | Quijano | A61B 17/11 606/153 |
| 5,830,224 | A | 11/1998 | Cohn et al. | |
| 5,840,081 | A * | 11/1998 | Andersen et al. | 623/1.11 |
| 5,855,601 | A * | 1/1999 | Bessler et al. | 623/2.38 |
| 5,957,949 | A * | 9/1999 | Leonhardt et al. | 623/1.24 |
| 5,961,440 | A | 10/1999 | Schweich, Jr. et al. | |
| 6,027,525 | A * | 2/2000 | Suh et al. | 623/1.1 |
| 6,045,497 | A | 4/2000 | Schweich, Jr. et al. | |
| 6,050,936 | A | 4/2000 | Schweich, Jr. et al. | |
| 6,059,715 | A | 5/2000 | Schweich, Jr. et al. | |
| 6,077,214 | A | 6/2000 | Mortier et al. | |
| 6,099,542 | A | 8/2000 | Cohn et al. | |
| 6,102,932 | A | 8/2000 | Kurz | |
| 6,162,168 | A | 12/2000 | Schweich, Jr. et al. | |
| 6,165,119 | A | 12/2000 | Schweich, Jr. et al. | |
| 6,168,614 | B1 * | 1/2001 | Andersen et al. | 623/1.26 |
| 6,183,411 | B1 | 2/2001 | Mortier et al. | |
| 6,210,432 | B1 | 4/2001 | Solem et al. | |
| 6,245,102 | B1 * | 6/2001 | Jayaraman | 623/1.15 |
| 6,254,564 | B1 * | 7/2001 | Wilk et al. | 604/9 |
| 6,261,222 | B1 | 7/2001 | Schweich, Jr. et al. | |
| 6,287,334 | B1 * | 9/2001 | Moll et al. | 623/1.24 |
| 6,287,339 | B1 * | 9/2001 | Vazquez et al. | 623/2.4 |
| 6,299,637 | B1 * | 10/2001 | Shaolian | A61F 2/2418 623/1.24 |
| 6,312,464 | B1 | 11/2001 | Navia | |
| 6,312,465 | B1 * | 11/2001 | Griffin et al. | 623/2.38 |
| 6,332,864 | B1 | 12/2001 | Schweich, Jr. et al. | |
| 6,332,893 | B1 | 12/2001 | Mortier et al. | |
| 6,338,735 | B1 | 1/2002 | Stevens | |
| 6,338,740 | B1 | 1/2002 | Carpentier | |
| 6,402,781 | B1 | 6/2002 | Langberg et al. | |
| 6,419,695 | B1 | 7/2002 | Gabbay | |
| 6,419,696 | B1 | 7/2002 | Ortiz et al. | |
| 6,425,916 | B1 * | 7/2002 | Garrison et al. | 623/2.11 |
| 6,440,164 | B1 | 8/2002 | DiMatteo et al. | |
| 6,454,799 | B1 | 9/2002 | Schreck | |
| 6,458,153 | B1 * | 10/2002 | Bailey et al. | 623/1.24 |
| 6,478,819 | B2 * | 11/2002 | Moe | 623/2.18 |
| 6,482,228 | B1 * | 11/2002 | Norred | 623/2.17 |
| 6,494,909 | B2 * | 12/2002 | Greenhalgh | 623/1.24 |
| 6,503,272 | B2 * | 1/2003 | Duerig | A61F 2/2418 623/1.24 |
| 6,514,194 | B2 | 2/2003 | Schweich, Jr. et al. | |
| 6,530,952 | B2 * | 3/2003 | Vesely | 623/2.18 |
| 6,537,198 | B1 | 3/2003 | Vidlund et al. | |
| 6,569,196 | B1 * | 5/2003 | Vesely | 623/2.14 |
| 6,582,462 | B1 * | 6/2003 | Andersen et al. | 623/1.26 |
| 6,602,286 | B1 * | 8/2003 | Strecker | A61F 2/2412 623/1.24 |
| 6,605,112 | B1 * | 8/2003 | Moll et al. | 623/1.24 |
| 6,616,684 | B1 | 9/2003 | Vidlund et al. | |
| 6,626,899 | B2 | 9/2003 | Houser et al. | |
| 6,629,534 | B1 | 10/2003 | St. Goar et al. | |
| 6,652,578 | B2 * | 11/2003 | Bailey et al. | 623/1.24 |
| 6,656,221 | B2 | 12/2003 | Taylor et al. | |
| 6,669,709 | B1 | 12/2003 | Cohn et al. | |
| 6,669,724 | B2 * | 12/2003 | Park et al. | 623/1.24 |
| 6,676,698 | B2 * | 1/2004 | McGuckin et al. | 623/1.24 |
| 6,676,699 | B2 | 1/2004 | Shiu | |
| 6,685,739 | B2 | 2/2004 | DiMatteo et al. | |
| 6,702,826 | B2 | 3/2004 | Liddicoat et al. | |
| 6,709,456 | B2 | 3/2004 | Langberg et al. | |
| 6,716,241 | B2 * | 4/2004 | Wilder et al. | 623/1.24 |
| 6,723,038 | B1 | 4/2004 | Schroeder et al. | |
| 6,752,828 | B2 * | 6/2004 | Thornton | A61F 2/2475 623/1.24 |
| 6,764,510 | B2 | 7/2004 | Vidlund et al. | |
| 6,773,454 | B2 * | 8/2004 | Wholey et al. | 623/1.15 |
| 6,790,237 | B2 * | 9/2004 | Stinson | 623/23.68 |
| 6,793,618 | B2 | 9/2004 | Schweich, Jr. et al. | |
| 6,821,297 | B2 | 11/2004 | Snyders | |
| 6,840,957 | B2 * | 1/2005 | DiMatteo et al. | 623/1.24 |
| 6,893,459 | B1 | 5/2005 | Macoviak | |
| 6,913,608 | B2 | 7/2005 | Liddicoat et al. | |
| 6,945,978 | B1 | 9/2005 | Hyde | |
| 6,951,571 | B1 * | 10/2005 | Srivastava | 623/1.24 |
| 6,974,474 | B2 * | 12/2005 | Pavcnik | A61F 2/07 623/1.24 |
| 6,979,350 | B2 * | 12/2005 | Moll et al. | 623/1.24 |
| 7,004,176 | B2 | 2/2006 | Lau | |
| 7,070,618 | B2 | 7/2006 | Streeter | |
| 7,125,418 | B2 * | 10/2006 | Duran et al. | 623/1.24 |
| 7,128,759 | B2 * | 10/2006 | Osborne et al. | 623/1.24 |
| 7,153,324 | B2 * | 12/2006 | Case et al. | 623/1.24 |
| 7,159,593 | B2 * | 1/2007 | McCarthy et al. | 128/898 |
| 7,160,320 | B2 | 1/2007 | Duran | 623/1.24 |
| 7,163,556 | B2 * | 1/2007 | Xie et al. | 623/2.14 |
| 7,166,126 | B2 * | 1/2007 | Spence et al. | 623/2.36 |
| 7,195,641 | B2 * | 3/2007 | Palmaz et al. | 623/2.18 |
| 7,201,772 | B2 * | 4/2007 | Schwammenthal et al. | 623/2.18 |
| 7,291,168 | B2 * | 11/2007 | Macoviak et al. | 623/2.36 |
| 7,311,730 | B2 * | 12/2007 | Gabbay | 623/2.38 |
| 7,338,520 | B2 * | 3/2008 | Bailey et al. | 623/1.24 |
| 7,347,869 | B2 * | 3/2008 | Hojeibane et al. | 623/1.24 |
| 7,351,256 | B2 * | 4/2008 | Hojeibane et al. | 623/1.24 |
| 7,377,938 | B2 * | 5/2008 | Sarac et al. | 623/1.26 |
| 7,381,220 | B2 * | 6/2008 | Macoviak et al. | 623/2.12 |
| 7,399,315 | B2 * | 7/2008 | Iobbi | 623/1.26 |
| 7,442,204 | B2 * | 10/2008 | Schwammenthal et al. | 623/1.24 |
| 7,452,371 | B2 * | 11/2008 | Pavcnik et al. | 623/1.24 |
| 7,458,987 | B2 * | 12/2008 | Case et al. | 623/1.24 |
| 7,503,928 | B2 * | 3/2009 | Case et al. | 623/1.24 |
| 7,524,331 | B2 * | 4/2009 | Birdsall | 623/2.11 |
| 7,527,646 | B2 * | 5/2009 | Rahdert et al. | 623/2.36 |
| 7,569,072 | B2 * | 8/2009 | Berg et al. | 623/2.38 |
| 7,604,661 | B2 * | 10/2009 | Pavcnik et al. | 623/1.24 |
| 7,611,534 | B2 * | 11/2009 | Kapadia et al. | 623/2.17 |
| 7,618,446 | B2 * | 11/2009 | Andersen et al. | 623/1.26 |
| 7,618,447 | B2 * | 11/2009 | Case et al. | 623/1.26 |
| 7,648,527 | B2 * | 1/2010 | Agnew | 623/1.24 |
| 7,670,368 | B2 * | 3/2010 | Hill et al. | 623/1.24 |
| 7,678,144 | B2 * | 3/2010 | Bailey et al. | 623/2.16 |
| 7,678,145 | B2 * | 3/2010 | Vidlund et al. | 623/2.36 |
| 7,682,390 | B2 * | 3/2010 | Seguin | 623/2.18 |
| 7,686,844 | B2 * | 3/2010 | Case et al. | 623/1.24 |
| 7,717,952 | B2 * | 5/2010 | Case et al. | 623/1.24 |
| 7,722,666 | B2 * | 5/2010 | Lafontaine | 623/2.11 |
| 7,748,389 | B2 * | 7/2010 | Salahieh et al. | 128/898 |
| 7,753,949 | B2 * | 7/2010 | Lamphere et al. | 623/1.26 |
| 7,799,069 | B2 * | 9/2010 | Bailey et al. | 623/1.26 |
| 7,803,185 | B2 * | 9/2010 | Gabbay | 623/2.11 |
| 7,806,921 | B2 * | 10/2010 | Hoffman | 623/1.24 |
| 7,815,673 | B2 * | 10/2010 | Bloom et al. | 623/1.15 |
| 7,837,727 | B2 * | 11/2010 | Goetz et al. | 623/2.18 |
| 7,846,199 | B2 * | 12/2010 | Paul et al. | 623/1.24 |
| 7,867,274 | B2 * | 1/2011 | Hill et al. | 623/1.24 |
| 7,871,434 | B2 * | 1/2011 | Case et al. | 623/2.12 |
| 7,896,915 | B2 * | 3/2011 | Guyenot et al. | 623/2.14 |
| 7,914,575 | B2 * | 3/2011 | Guyenot et al. | 623/2.14 |
| 7,947,075 | B2 * | 5/2011 | Goetz et al. | 623/2.18 |
| 7,951,189 | B2 * | 5/2011 | Haverkost et al. | 623/1.24 |
| 7,955,375 | B2 * | 6/2011 | Agnew | 623/1.24 |
| 7,955,377 | B2 * | 6/2011 | Melsheimer | 623/1.24 |
| 7,959,670 | B2 * | 6/2011 | Bolduc | 623/1.36 |
| 7,967,853 | B2 * | 6/2011 | Eidenschink et al. | 623/1.24 |
| 8,002,824 | B2 * | 8/2011 | Jenson et al. | 623/2.12 |
| 8,012,198 | B2 * | 9/2011 | Hill et al. | 623/1.24 |
| 8,016,882 | B2 * | 9/2011 | Macoviak et al. | 623/2.36 |
| 8,038,708 | B2 * | 10/2011 | Case et al. | 623/1.24 |
| 8,043,360 | B2 * | 10/2011 | McNamara et al. | 623/1.15 |
| 8,048,153 | B2 * | 11/2011 | Salahieh et al. | 623/2.11 |
| 8,052,749 | B2 * | 11/2011 | Salahieh et al. | 623/2.17 |
| 8,057,532 | B2 * | 11/2011 | Hoffman | 623/1.24 |

(56) References Cited

U.S. PATENT DOCUMENTS

| | | | |
|---|---|---|---|
| 8,070,802 B2* | 12/2011 | Lamphere et al. | 623/2.14 |
| 8,075,611 B2* | 12/2011 | Millwee et al. | 623/1.24 |
| 8,092,518 B2* | 1/2012 | Schreck | 623/1.26 |
| 8,092,520 B2* | 1/2012 | Quadri | 623/1.36 |
| 8,100,962 B2* | 1/2012 | Agnew et al. | 623/1.24 |
| 8,109,996 B2* | 2/2012 | Stacchino et al. | 623/2.17 |
| 8,118,866 B2* | 2/2012 | Herrmann et al. | 623/2.11 |
| 8,128,681 B2* | 3/2012 | Shoemaker et al. | 623/1.24 |
| 8,133,270 B2* | 3/2012 | Kheradvar et al. | 623/2.11 |
| 8,142,494 B2* | 3/2012 | Rahdert et al. | 623/2.36 |
| 8,182,528 B2* | 5/2012 | Salahieh et al. | 623/2.11 |
| 8,216,303 B2* | 7/2012 | Navia | 623/2.36 |
| 8,226,707 B2* | 7/2012 | White | 623/1.24 |
| 8,231,670 B2* | 7/2012 | Salahieh et al. | 623/2.11 |
| 8,246,678 B2* | 8/2012 | Salahieh et al. | 623/2.11 |
| 8,252,052 B2* | 8/2012 | Salahieh et al. | 623/2.18 |
| 8,287,584 B2* | 10/2012 | Salahieh et al. | 623/1.11 |
| 8,308,798 B2* | 11/2012 | Pintor et al. | 623/2.18 |
| 8,328,868 B2* | 12/2012 | Paul et al. | 623/2.11 |
| 8,343,213 B2* | 1/2013 | Salahieh et al. | 623/2.11 |
| 8,403,979 B2* | 3/2013 | Paul, Jr. | A61F 2/2412 623/1.24 |
| 8,414,641 B2* | 4/2013 | Stocker et al. | 623/1.24 |
| 8,454,684 B2* | 6/2013 | Bergin et al. | 623/2.11 |
| 8,460,365 B2* | 6/2013 | Haverkost et al. | 623/1.24 |
| 2001/0010017 A1 | 7/2001 | Letac et al. | |
| 2001/0021872 A1* | 9/2001 | Bailey et al. | 623/1.24 |
| 2001/0051824 A1 | 12/2001 | Hopkins et al. | |
| 2002/0032481 A1* | 3/2002 | Gabbay | 623/2.11 |
| 2002/0065554 A1* | 5/2002 | Streeter | 623/2.36 |
| 2002/0094573 A1 | 7/2002 | Bell | |
| 2002/0123802 A1 | 9/2002 | Snyders | |
| 2002/0129820 A1 | 9/2002 | Ryan et al. | |
| 2002/0138138 A1* | 9/2002 | Yang | 623/2.18 |
| 2003/0014104 A1* | 1/2003 | Cribier | 623/2.11 |
| 2003/0040792 A1* | 2/2003 | Gabbay | 623/2.11 |
| 2003/0120340 A1 | 6/2003 | Liska et al. | |
| 2003/0233022 A1 | 12/2003 | Vidlund et al. | |
| 2004/0127981 A1* | 7/2004 | Rahdert et al. | 623/2.36 |
| 2004/0138745 A1* | 7/2004 | Macoviak et al. | 623/2.36 |
| 2004/0148019 A1* | 7/2004 | Vidlund et al. | 623/2.36 |
| 2004/0243107 A1* | 12/2004 | Macoviak et al. | 606/1 |
| 2005/0010287 A1* | 1/2005 | Macoviak et al. | 623/2.36 |
| 2005/0055089 A1* | 3/2005 | Macoviak et al. | 623/2.37 |
| 2005/0228468 A1* | 10/2005 | Macoviak et al. | 607/119 |
| 2005/0245906 A1 | 11/2005 | Makower et al. | |
| 2005/0267573 A9* | 12/2005 | Macoviak et al. | 623/2.36 |
| 2006/0069430 A9* | 3/2006 | Rahdert et al. | 623/2.36 |
| 2006/0241745 A1* | 10/2006 | Solem | 623/2.18 |
| 2008/0065204 A1* | 3/2008 | Macoviak et al. | 623/2.17 |
| 2008/0140190 A1* | 6/2008 | Macoviak et al. | 623/2.36 |
| 2009/0005763 A1 | 1/2009 | Makower et al. | |
| 2009/0043381 A1* | 2/2009 | Macoviak et al. | 623/2.36 |
| 2009/0228099 A1* | 9/2009 | Rahdert et al. | 623/2.37 |
| 2011/0319990 A1* | 12/2011 | Macoviak et al. | 623/2.11 |
| 2012/0185040 A1* | 7/2012 | Rahdert et al. | 623/2.36 |
| 2013/0079869 A1* | 3/2013 | Straubinger et al. | 623/1.26 |
| 2013/0096664 A1* | 4/2013 | Goetz et al. | 623/1.11 |
| 2013/0123908 A1* | 5/2013 | Hinchliffe et al. | 623/1.24 |
| 2013/0178929 A1* | 7/2013 | Nakayama et al. | 623/1.24 |

OTHER PUBLICATIONS

Moore et al. "Unsuitability of Transventricular Autogenous Slings for Diminishing Valvular Insufficiency", Surgery vol. 33, No. 2, Feb. 1953 pp. 173-182.

Murray et al., "Reconstruction of the Valves of the Heart", The Canadian Medical Association Journal, vol. 38, No. 4, Apr. 1938 pp. 317-319.

Bolling et al., "Early Outcome of Mitral Valve Reconstruction in Patients with End-Stage Cardiomyopathy", J Thorac Cardiovasc Surg, 1995; 109;676-683.

Kameda et al. "Annuloplasty for Severe Mitral Regurgitation Due to Dilated Cardiomyopathy", Ann. Thorac. Surg 1996; 61:1829-1832.

Harlan et al. Manual of Cardiac Surgery, vol. 2 1981, Figs 16.3-16.4.

Edmunds Jr. et al., "Septal Defect" Atlas of Cardiothoracic Surgery 1990.

Koniaris et al. "Dynamic Retention: A Technique for Closure of the Complex Abdomen in Critically Ill Patients", Archives of Surgery, vol. 136, No. 12, Dec. 2001; pp. 1359-1362.

Fucci et al. "Improved Results with Mitral Valve Repair Using New Surgical Technniques", European Journal of Cardio-Thoracic Surgery, vol. 9 1996; pp. 621-626.

Wilson, "Studies in Experimental Mitral Obstruction in Relation to the Surgical Treatment of Mitral Stenosis", The British Journal of Surgery, Vo. 18, No. 70, 1931, pp. 259-274.

Bailey et al., "Surgical Repair of Mitral Insufficiency", Diseases of the Chest, vol. XIX, No. 2, Feb. 1951; pp. 125-137.

Henderson et al., "The Surgical Treatment of Mitral Insufficiency", Experimental Use of Transplanted Pericardium in Dogs, Surgery 33(6)858-868; 1953.

Sakakibara "A Surgical Approach to the Correction of Mitral Insufficiency", Annals of Surgery, vol. 142, No. 2, Aug. 1955; pp. 196-203.

Harken et al., "The Surgical Correction of Mitral Insuificciency", The Journal of Thoracic Surgery 28(6):604-627; 1954.

Bailey et al. "The Surgical Correction of Mitral Insufficnecy by the Use of Pericardial Grafts", The Journal of Thoracic Surgery, vol. 28, No. 6, Dec. 1954; pp. 551-603.

Kay et al. "Surgical Treatment of Mitral Insufficiency", Sugery, vol. 37, No. 5, May 1955; pp. 697-706.

de Silva et al "Postinfarction Ventricular Septal Defect. An Efficacious Technique for Early Surgical Repair", J. Thorac Cardiovasc Surg. Jan. 1989; 97(1):86-9.

Tashiro et al. "Extended Endocardial Repair of Postinfarction Ventricular Septal Rupture: New Operative Technique", J Card Surg Mar. 1994; 9(2)97-102.

Daggett, "Surgical Technique for Early Repair of Posterior Ventricular Septal Rupture" J Thorac Cardiovasc Surg. Aug. 1982 84(2)306-12.

Daggett et al. "Surgery for Post-Myocardial Infarct Ventricular Septal Defect". Ann Surg. Sep. 1977, 186(3): 260-71.

Dor, "Left Ventricular Aneurysms: The Endoventricular Circular Patch Plasty", Semin Thorac Cardiovasc Surg. Apr. 1997; 9(2):123-30.

Antunes "Submitral Left Ventricular Aneurysms. Correction by a New Transatrial Approach", J Thorac Cardiovasc Surg Aug. 1987; 94(2):241-5.

Alvarez et al. "Technical Improvements in the Repair of Acute Postinfarction Ventricular Septal Rupture", J Card Surg. Sep. 1992; 7(3):198-202.

Cox, "Surg Manage. of Left Vent Aneurysms" A Clarification of the Simil. and Diff. Between the Jatene and Dor Techniques Semin Thorac Cardiovsc Surg Apr. 1997 9(2):131-8.

Skillington et al. "Surg. Treat. for Infarct-Related Ventr. Septal Def. Improved Early Res. Comb w/Analysis of Late Func. Stat." J Thorac Cardiovasc Surg May 1990 99(5) 798-808.

Salati et al., "Severe Diastolic Dysfunction After Endoventriculoplasty" J Thorac Cardiovasc Surg Apr. 1995, 109(4): 694-701.

Davila et al. "Circumfential Suture of the Mitral Ring: A Method for the Surg. Correction of Mitral Insufficiency" Jour of Thorac Surg. Nov. 1955; 30(5); 531-60.

Harken etal. "The Surgical Correction of Mitral Insufficiency" Jour of Thorac Surgery Dec. 1954; 28(6): 604-24.

Kuykendall et al. "Surgical Correction of Chronic Mitral Insufficiency in Dogs", Surgery. Oct. 1958; 44(4) 718-25.

Davila et al. "A Method for the Surgical Correction of Mitral Insufficiency", Surg. Gyno. & Obstetrics, Apr. 1954, 98(4): 407-12.

Glover et al., "The Treatment of Mitral Insufficiency by the Purse-String Technique", Jour of Thorac Surg. Jan. 1957; 33(1): 75-101.

Rankin et al. "A Clinical Comparison of Mitral Valve Repair vs Valve Replacmeent in Ischemic Mitral Regurgitation", J. Thorac. Cardio. Surg. Feb. 1988; 95(2): 165-77.

(56) References Cited

OTHER PUBLICATIONS

Harken et al. "The Surgical Correction of Mitral Insufficiency", Surg. Forum 4:4-7, 1953.
Davila et al "The Clinical & Physiologic Criteria for Surgical Correction of Mitral Insufficiency" Jour of Thorac Surg. Feb. 1958; 35(2):208-31.
Barnard et al. "A Surgical Approach to Mitral Insufficiency" Br J Surg. May 1961; 48:655-62.
McKenzie et al. "Current Concepts in Surgical Correction of Acquired Mitral Insufficiency" Circulation, Oct. 1963; 28:603-16.
Saab et al., "Left Ventricular Aneurysm: A New Surgical Approach", Thorac Cardiovasc Surg, Feb. 1989; 37(1):11-9.
Cicek et al. "Left Ventricular Endoan: Effect on Left Ventricular Size, Shape and Function", Cardiology, Jul.-Aug. 1997, 88(4)340-5.
Liedtke et al., "Functional Reductions in Left Ventricular Volume" Jour Thorac Cardio. Surg. Feb. 1976; 71(2)195-206.
Sosa et al., Recurrent Ventricular Tachycardia Assoc with Postinfarction Aneurysm Results of Left Ventricular Reconstruction, Jour Thorac Cardio Surg. May 1992, 103(5)855-60.
Cooley, "Repair of Postinfarction Ventricular Septal Defect" Jour Card Surg. Jul. 1994 9:4):427-9.
Jatene, "Left Ventricular Aneurysmectomy Resection or Reconstruction", Jour Thorac Card. Surg. 1985; 89:321-31.
Wilson, "Studies in Experimental Mitral Obstruction in Relation to the Surgical Treatment of Mitral Stenosis", The British Journal of Surgery; vol. XVIII No. 70:259-74; 1931.
Yacoub et al. "Anatomic Correction of the Syndrome of Prolapsing Right Coronary Aortic Cusp . . . ", Journal of Thoracic and Cardiovascular Surgery, Feb. 1997: 113(2): 253-261.

\* cited by examiner

DEVICES, SYSTEMS, AND METHODS FOR SUPPLEMENTING, REPAIRING OR REPLACING A NATIVE HEART VALVE LEAFLET

RELATED APPLICATIONS

This application is a divisional of application Ser. No. 11/981,025 filed 31 Oct. 2007 (now U.S. Pat. No. 8,016,882), which is a divisional of application Ser. No. 10/676,815, filed Oct. 1, 2003.

FIELD OF THE INVENTION

The invention is directed to devices, systems, and methods for improving the function of a heart valve, e.g., in the treatment of mitral valve regurgitation.

BACKGROUND OF THE INVENTION

I. The Anatomy of a Healthy Heart

The heart (see FIG. 1) is slightly larger than a clenched fist. It is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side—the right and left atria, and the right and left ventricles.

The atria are the blood-receiving chambers, which pump blood into the ventricles. A wall composed of membranous and muscular parts, called the interatrial septum, separates the right and left atria. The ventricles are the blood-discharging chambers. A wall composed of membranous and muscular parts, called the interventricular septum, separates the right and left ventricles.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves (see FIGS. 2 and 3) that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of ventricular diastole (i.e., ventricular filling) (see FIG. 2), the aortic and pulmonary valves are closed to prevent back flow from the arteries into the ventricles. Shortly thereafter, the tricuspid and mitral valves open (as FIG. 2 shows), to allow flow from the atria into the corresponding ventricles. Shortly after ventricular systole (i.e., ventricular emptying) begins, the tricuspid and mitral valves close (see FIG. 3)—to prevent back flow from the ventricles into the corresponding atria—and the aortic and pulmonary valves open—to permit discharge of blood into the arteries from the corresponding ventricles.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

FIG. 4 shows a posterior oblique cutaway view of a healthy human heart 100. Two of the four heart chambers are shown, the left atrium 170, and the left ventricle 140 (not shown are the right atrium and right ventricle). The left atrium 170 fills with blood from the pulmonary veins. The blood then passes through the mitral valve (also known as the bicuspid valve, and more generally known as an atrio-ventricular valve) during ventricular diastole and into the left ventricle 140. During ventricular systole, the blood is then ejected out of the left ventricle 140 through the aortic valve 150 and into the aorta 160. At this time, the mitral valve should be shut so that blood is not regurgitated back into the left atrium.

The mitral valve consists of two leaflets, an anterior leaflet 110, and a posterior leaflet 115, attached to chordae tendineae 120 (or chords), which in turn are connected to papillary muscles 130 within the left atrium 140. Typically, the mitral valve has a D-shaped anterior leaflet 110 oriented toward the aortic valve, with a crescent shaped posterior leaflet 115. The leaflets intersect with the atrium 170 at the mitral annulus 190.

In a healthy heart, these muscles and their chords support the mitral and tricuspid valves, allowing the leaflets to resist the high pressure developed during contractions (pumping) of the left and right ventricles. In a healthy heart, the chords become taut, preventing the leaflets from being forced into the left or right atria and everted. Prolapse is a term used to describe the condition wherein the coaptation edges of each leaflet initially may coapt and close, but then the leaflets rise higher and the edges separate and the valve leaks. This is normally prevented by contraction of the papillary muscles and the normal length of the chords. Contraction of the papillary muscles is simultaneous with the contraction of the ventricle and serves to keep healthy valve leaflets tightly shut at peak contraction pressures exerted by the ventricle.

II. Characteristics and Causes of Mitral Valve Dysfunction

Valve malfunction can result from the chords becoming stretched, and in some cases tearing. When a chord tears, the result is a flailed leaflet. Also, a normally structured valve may not function properly because of an enlargement of the valve annulus pulling the leaflets apart. This condition is referred to as a dilation of the annulus and generally results from heart muscle failure. In addition, the valve may be defective at birth or because of an acquired disease, usually infectious or inflammatory.

FIG. 5 shows a cutaway view of a human heart 200 with a prolapsed mitral valve. The prolapsed valve does not form a tight seal during ventricular systole, and thus allows blood to be regurgitated back into the left atrium during ventricular contraction. The anterior 220 and posterior 225 leaflets are shown rising higher than normal (i.e., prolapsing) into the left atrium. The arrows indicate the direction of regurgitant flow. Among other causes, regurgitation can result from redundant valve leaflet tissue or from stretched chords 210 that are too long to prevent the leaflets from being blown into the atrium. As a result, the leaflets do not form a tight seal, and blood is regurgitated into the atrium.

FIG. 6 shows a cutaway view of a human heart 300 with a flailing mitral valve 320. The flailing valve also does not form a tight seal during ventricular systole. Blood thus regurgitates back into the left atrium during ventricular contraction, as indicated by the arrows. Among other causes, regurgitation can also result from torn chords 310. As an example, FIG. 7 shows a cutaway view of a human heart where the anterior leaflet 910 has torn chords 920. As a result, valve flailing and blood regurgitation occur during ventricular systole.

As a result of regurgitation, "extra" blood back flows into the left atrium. During subsequent ventricular diastole (when the heart relaxes), this "extra" blood returns to the left ventricle, creating a volume overload, i.e., too much blood in the left ventricle. During subsequent ventricular systole (when the heart contracts), there is more blood in the ventricle than expected. This means that: (1) the heart must pump harder to move the extra blood; (2) too little blood may move from the heart to the rest of the body; and (3) over time, the left ventricle may begin to stretch and enlarge to accommodate the larger volume of blood, and the left ventricle may become weaker.

Although mild cases of mitral valve regurgitation result in few problems, more severe and chronic cases eventually weaken the heart and can result in heart failure. Mitral valve regurgitation can be an acute or chronic condition. It is sometimes called mitral insufficiency.

III. Prior Treatment Modalities

In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

To date, invasive, open heart surgical approaches have been used to repair or replace the mitral valve with either a mechanical valve or biological tissue (bioprosthetic) taken from pigs, cows, or horses.

The need remains for simple, cost-effective, and less invasive devices, systems, and methods for treating dysfunction of a heart valve, e.g., in the treatment of mitral valve regurgitation.

SUMMARY OF THE INVENTION

The invention provides devices, systems and methods that supplement, repair, or replace a native heart valve leaflet. The devices, systems, and methods include an implant that, in use, rests adjacent a valve annulus.

The implant defines a pseudo-annulus. The implant includes a neoleaflet element that occupies the space of at least a portion of one native valve leaflet. The implant allows the native leaflets to coexist with the implant, or if desired or indicated, one or more native leaflets can be removed and replaced by the implant. The neoleaflet element of the implant is shaped and compressed to mimic the one-way valve function of a native leaflet. The implant includes spaced-apart struts that are sized and configured to contact tissue near or within the heart valve annulus to brace the implant against migration within the annulus during the one-way valve function.

According to one aspect of the invention, the implant includes a scaffold, which defines a pseudo-annulus. The implant further includes at least two struts in generally oppositely spaced apart positions on the scaffold. The scaffold can be placed in an elastically loaded condition in a heart with the struts engaging tissue at or near the leaflet commissures of a heart valve annulus, to reshape the annulus for leaflet coaptation. The implant further provides a neoleaflet element coupled to the scaffold within pseudo-annulus, to provide a one-way valve function.

Other features and advantages of the invention shall be apparent based upon the accompanying description, drawings, and claims.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

Figure 1:
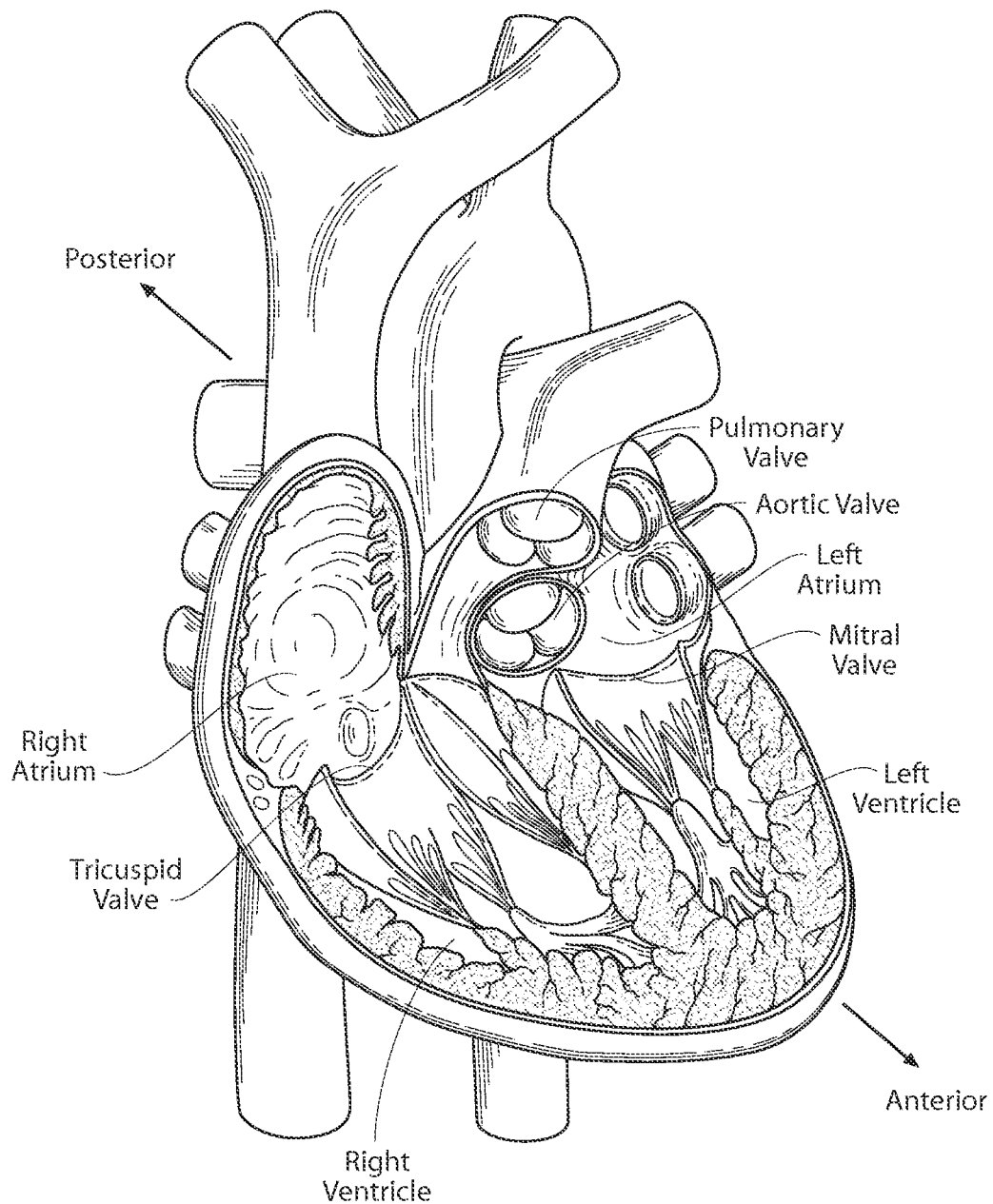
FIG. 1 is a perspective, anterior anatomic view of the interior of a healthy heart.
Figure 2:
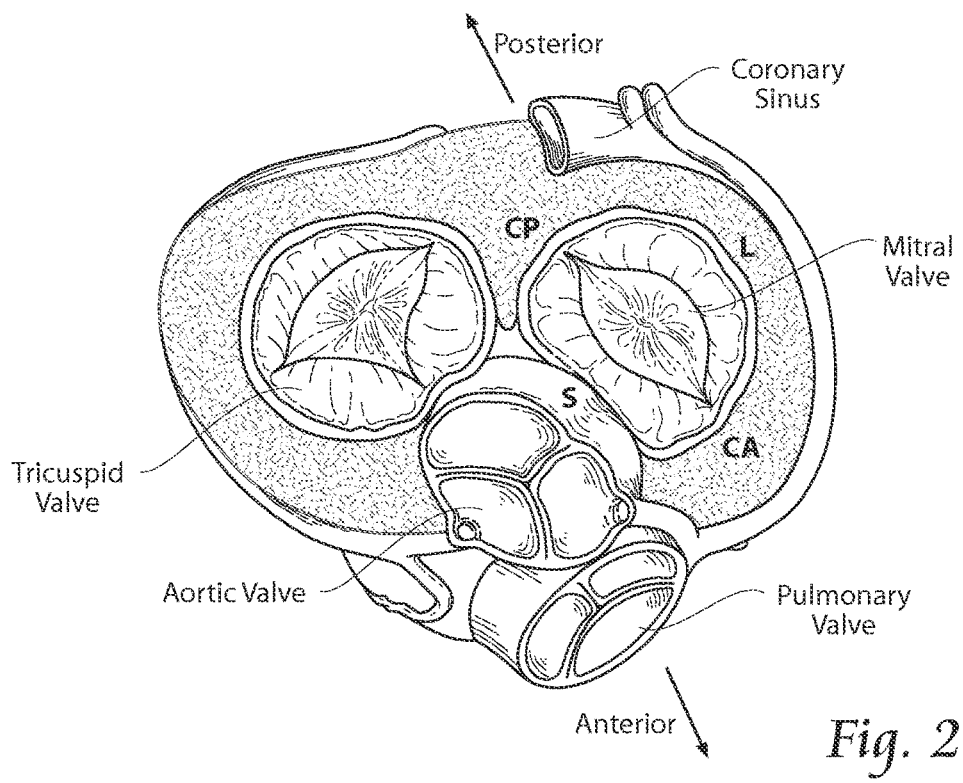
FIG. 2 is a superior anatomic view of the interior of a healthy heart, with the atria removed, showing the condition of the heart valves during ventricular diastole.
Figure 3:
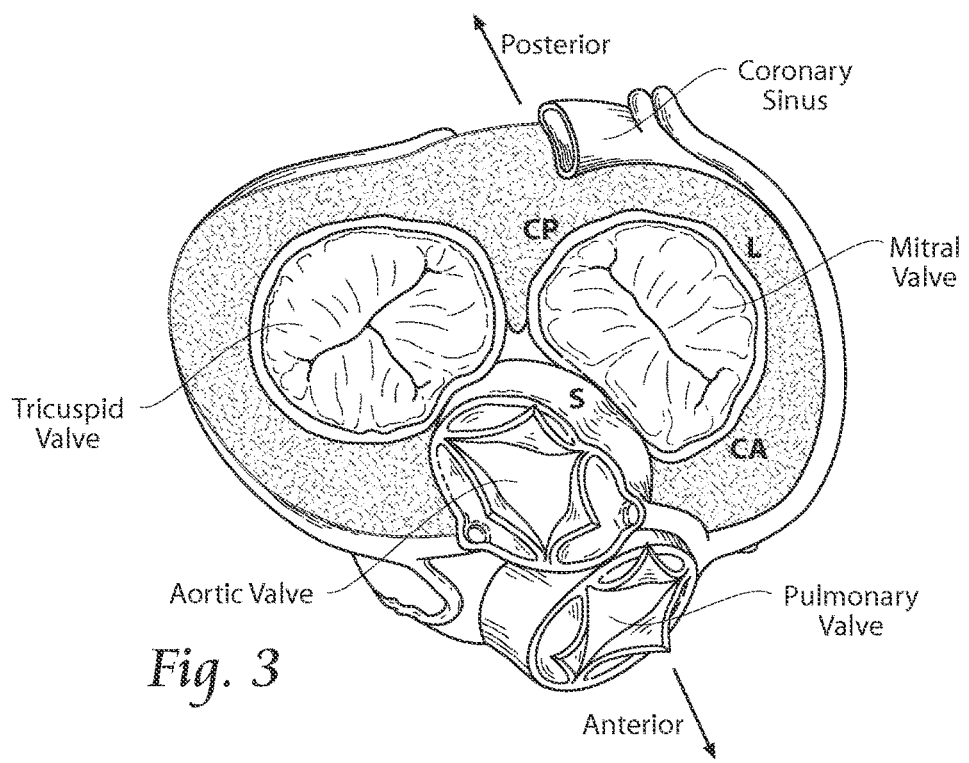
FIG. 3 is a superior anatomic view of the interior of a healthy heart, with the atria removed, showing the condition of the heart valves during ventricular systole.
Figure 4:
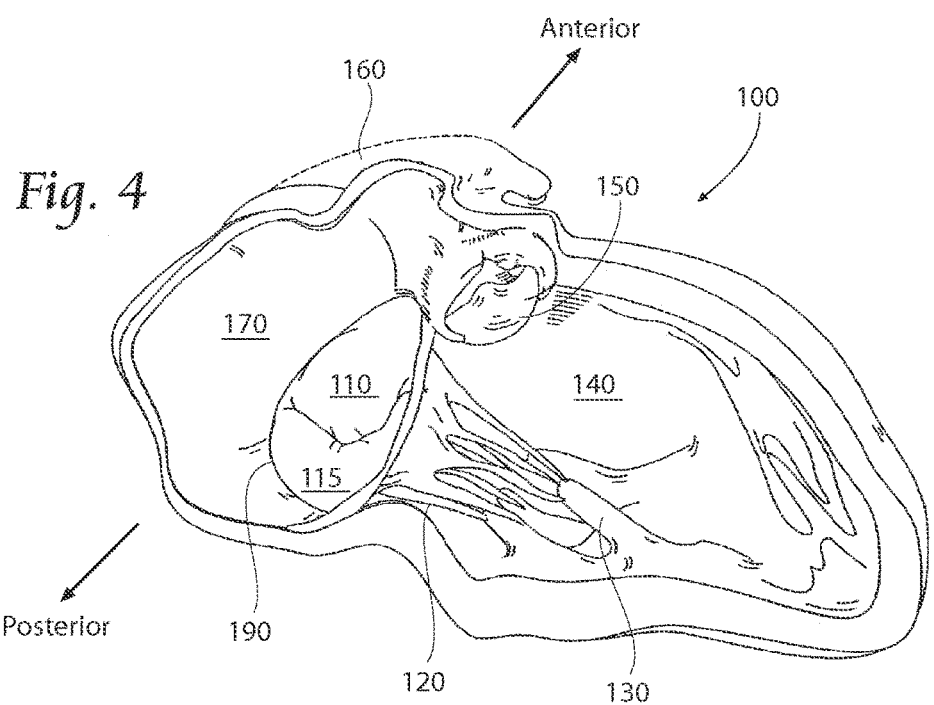
FIG. 4 is a posterior oblique cutaway view of a portion of a human heart, showing a healthy mitral valve during ventricular systole, with the leaflets properly coapting.
Figure 5:
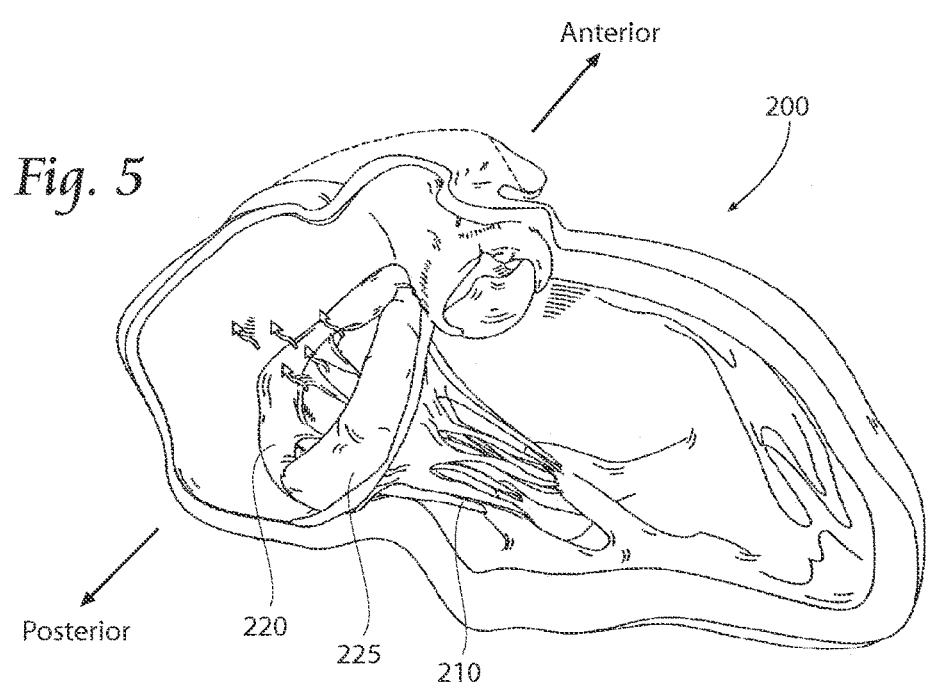
FIG. 5 is a posterior oblique cutaway view of a portion of a human heart, showing a dysfunctional prolapsing mitral valve during ventricular systole, with the leaflets not properly coapting, causing regurgitation.
Figure 6:
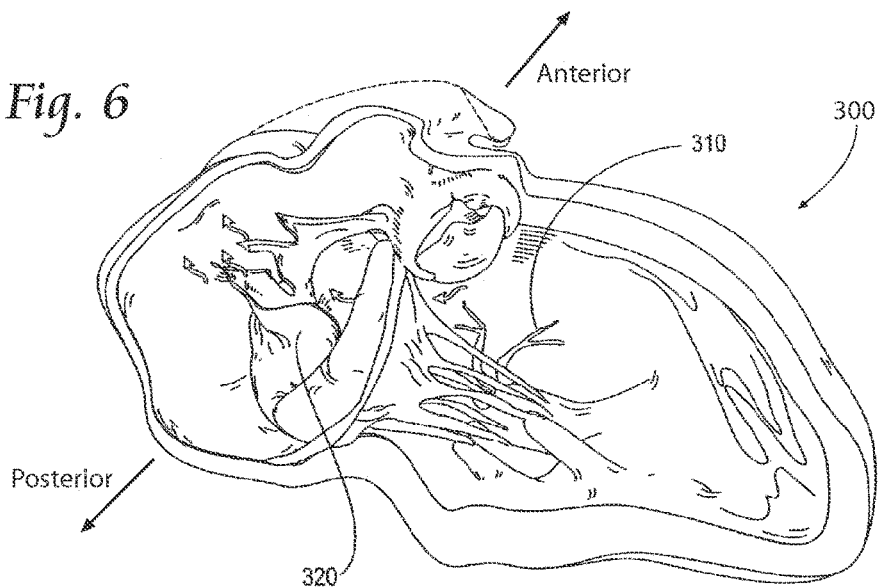
FIG. 6 is a posterior oblique cutaway view of a portion of a human heart, showing a dysfunctional mitral valve during ventricular systole, with the leaflets flailing, causing regurgitation.
Figure 7:
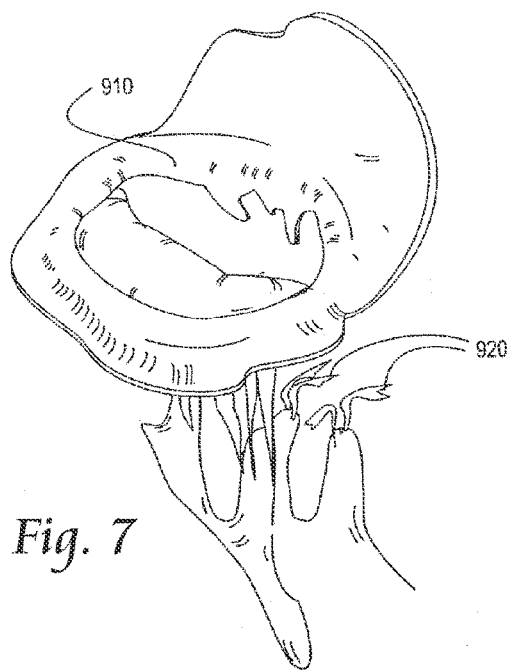
FIG. 7 is a posterior oblique cutaway view of a portion of a human heart, showing a dysfunctional mitral valve during ventricular systole, caused by torn chords, that leads to regurgitation.
Figure 8:
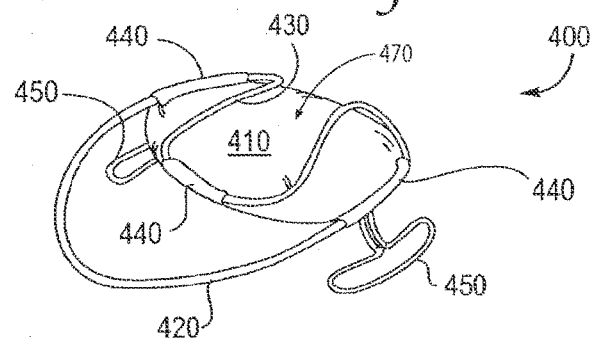
FIG. 8 is a perspective view of an implant that supplements, repairs, or replaces a native heart valve leaflet, the implant being sized and configured to extend about a heart valve annulus and including a neoleaflet element that occupies the space of at least one native valve leaflet.

FIGS. 8 and 9 show an implant 400 sized and configured to supplement, repair, or replace a dysfunctional native heart valve leaflet or leaflets. In use (see, in particular, FIG. 9), the implant 400 defines a pseudo-annulus that rests adjacent the native valve annulus and includes a neoleaflet element that occupies the space of at least a portion of one native valve leaflet. The implant 400 allows the native leaflets to coexist with the implant 400. If desired or indicated, one or more native leaflets can be removed and replaced by the implant 400.

In its most basic form, the implant 400 is made—e.g., by machining, bending, shaping, joining, molding, or extrusion—from a biocompatible metallic or polymer material, or a metallic or polymer material that is suitably coated, impregnated, or otherwise treated with a material to impart biocompatibility, or a combination of such materials. The material is also desirably radio-opaque to facilitate fluoroscopic visualization.

As FIG. 8 shows, the implant 400 includes a base or scaffold 420 that, in the illustrated embodiment, is sized and configured to rest adjacent the mitral annulus. At least a portion of the base 420 forms an annular body that approximates the shape of the native annulus. For this reason, the base 420 will also be referred to as a "pseudo-annulus."

Figure 9A:
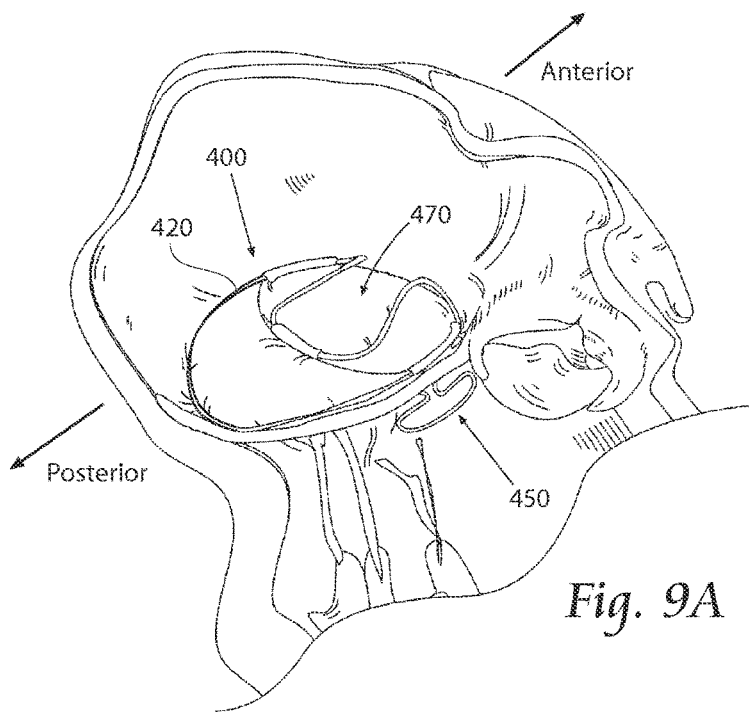
FIG. 9A is a perspective, anatomic view of the implant shown in FIG. 8, with the neoleaflet element installed over an anterior leaflet of a mitral valve to restore normal function.
Figure 9B:
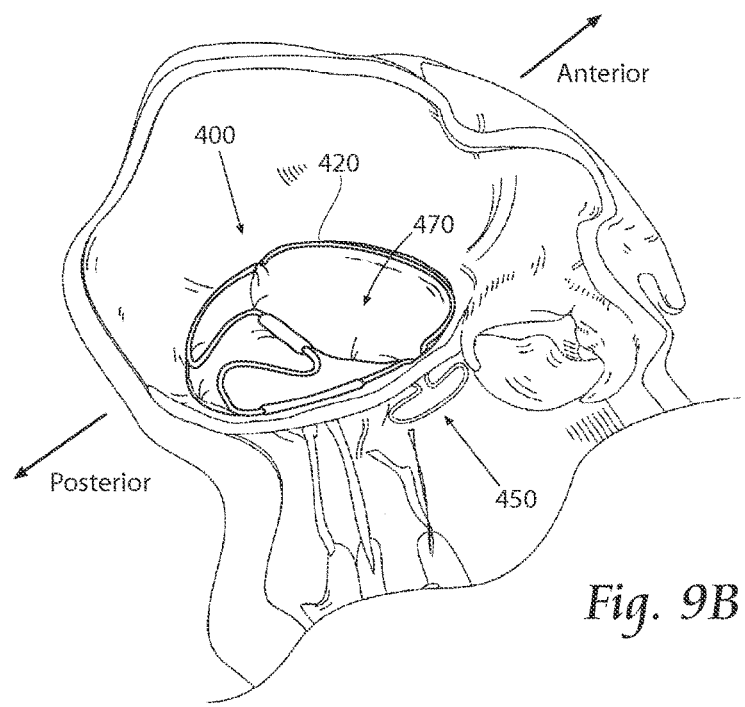
FIG. 9B is a perspective, anatomic view of the implant of the type shown in FIG. 8, with the neoleaflet element installed over a posterior leaflet of a mitral valve to restore normal function to the native valve leaflet.

The base 420 supports a bridge 430 that extends into the valve. The bridge 430 is sized and configured (see FIG. 9A) to overlay the space of at least a portion of one native valve leaflet. In FIG. 9A, the bridge 430 overlays an anterior leaflet. However, as FIG. 9B shows, the bridge 430 could be oriented to overlay a posterior leaflet. As will be described later (see FIG. 11), two bridges can be formed to overlay both leaflets.

As FIG. 8 shows, the implant 400 includes a material 410 that covers or spans the bridge 430. The spanning material 410 may be attached to the implant 400 with one or more attachment means 440. For example, the spanning materials 410 may be sewn, glued, or welded to the implant 400, or it may be attached to itself when wrapped around the implant 400. The spanning material 410 may be made from a synthetic material (for example, thin Nitinol, polyester fabric, polytetrafluoroethylene or PTFE, silicone, or polyurethane) or a biological material (for example, human or animal pericardium).

Together, the bridge 430 and the spanning material 410 comprise a neoleaflet element 470 coupled to the base 420. The neoleaflet element 470 may be rigid, semi-rigid, or flexible. The neoleaflet element 470 is coupled to the base 420 in a manner that exerts a mechanical, one-way force to provide a valve function that responds to differential pressure conditions across the neoleaflet element. In response to one prescribed differential pressure condition, the neoleaflet element 470 will deflect and, with a native leaflet, assume a valve opened condition. In response to another prescribed pressure condition, the neoleaflet element 470 will resist deflection and, by coaptation with a native leaflet (or a companion neoleaflet element) at, above, or below the annulus plane, maintain a valve closed condition.

In the context of the illustrated embodiment (when installed in a mitral valve annulus), the neoleaflet element resists being moved in the cranial (superior) direction (into the atrium), when the pressure in the ventricle exceeds the pressure in the atrium—as it would during ventricular systole. The neoleaflet element 470 may move, however, in the caudal (inferior) direction (into the ventricle), when the pressure in the ventricle is less than the pressure in the atrium—as it would during ventricular diastole. The neoleaflet element 470 thereby mimics the one-way valve function of a native leaflet, to prevent retrograde flow.

The implant 400 is sized and shaped so that, in use adjacent the valve annulus of the mitral valve, it keeps the native valve leaflet closed during ventricular systole (as shown in FIGS. 9A and 9B), to prevent flailing and/or prolapse of the native valve leaflet it overlays during ventricular systole. The implant 400 thus restores to the heart valve leaflet or leaflets a normal resistance to the high pressure developed during ventricular contractions, resisting valve leaflet eversion and/or prolapse and the resulting back flow of blood from the ventricle into the atrium during ventricular systole. The pressure difference serves to keep valve leaflets tightly shut during ventricular systole. The implant 400, however, does not interfere with opening of the native valve leaflet or leaflets during ventricular diastole (see, e.g., FIG. 12). The implant 400 allows the leaflet or leaflets to open during ventricular diastole, so that blood flow occurs from the atrium into the ventricle. The implant 400 thereby restores normal one-way function to the valve, to prevent retrograde flow.

The functional characteristics of the implant 400 just described can be imparted to the neoleaflet element 470 in various ways. For example, hinges and springs (mechanical or plastic) can be used to couple the bridge to the base. Desirably, the implant 400 is made from materials that provide it with spring-like characteristics.

As shown in FIG. 8, in the illustrated embodiment, the base 420 and bridge 430 are shaped from a length of wire-formed material. The shape and material properties of the implant determine its physical spring-like characteristics as well as its ability to open in one direction only. The spring-like characteristics of the implant 400 allow it to respond dynamically to changing differential pressure conditions within the heart.

Figure 12:
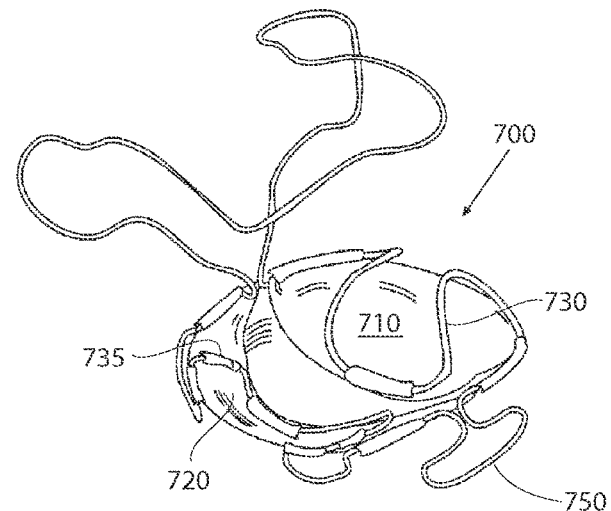
FIG. 12 is a perspective view of the implant shown in FIG. 11, with the two neoleaflet elements in a valve opened condition, as would exist during ventricular diastole.

More particularly, in the illustrated mitral valve embodiment, when greater pressure exists superior to the bridge 430 than inferior to the bridge (i.e., during ventricular diastole), the shape and material properties of the bridge 430 accommodate its deflection into the ventricle—i.e., an opened valve condition (as FIG. 12 shows in another illustrative embodiment). When greater pressure exists inferior to the bridge 430 than superior to the bridge (i.e., during ventricular systole), the shape and material properties of the bridge 430 enable it to resist superior movement of the leaflet into the atrium, and otherwise resist eversion and/or prolapse of the valve leaflet into the atrium (as FIGS. 9A and 9B also show).

The implant 400 may be delivered percutaneously, thoracoscopically through the chest, or using open heart surgical techniques. If delivered percutaneously, the implant 400 may be made from a superelastic material (for example superelastic Nitinol alloy) enabling it to be folded and collapsed such that it can be delivered in a catheter, and will subsequently self-expand into the desired shape and tension when released from the catheter.

Figure 21A:
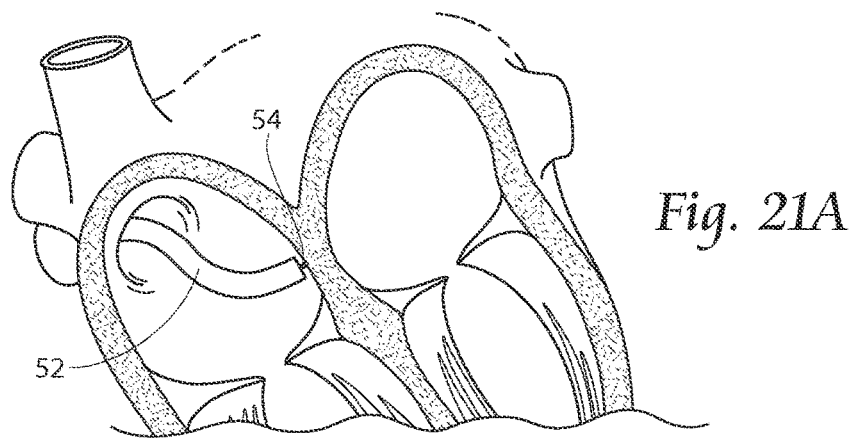
FIGS. 21A to 21C diagrammatically show a method of gaining intravascular access to the left atrium for the purpose of deploying a delivery catheter to place an implant in a valve annulus to supplement, repair, or replace a native heart valve leaflet
Figure 21B:
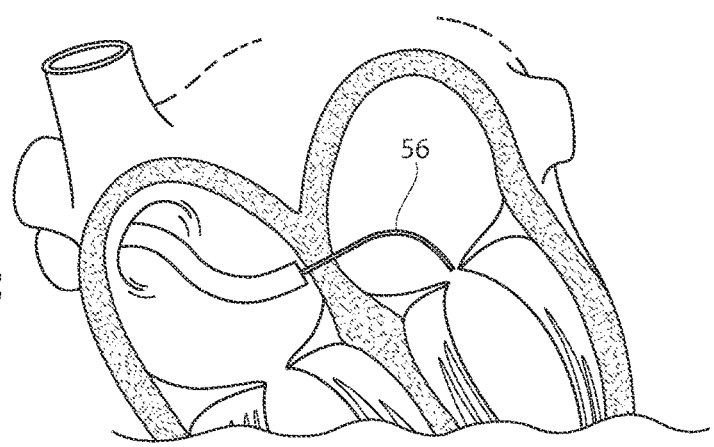
Figure 21C:
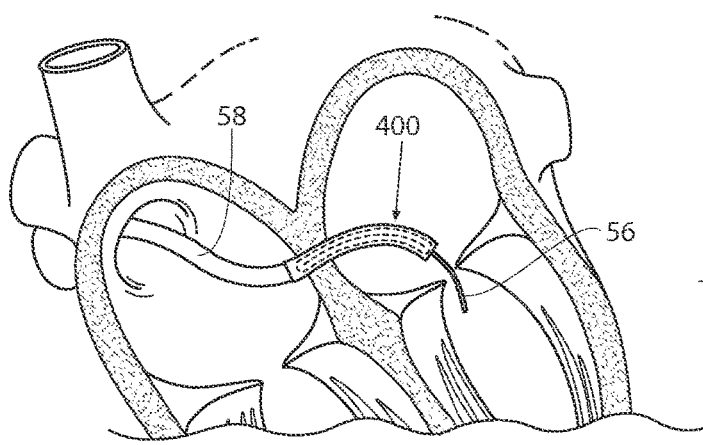

For example, percutaneous vascular access can be achieved by conventional methods into the femoral or jugular vein. As FIG. 21A shows, under image guidance (e.g., fluoroscopic, ultrasonic, magnetic resonance, computed tomography, or combinations thereof), a catheter 52 is steered through the vasculature into the right atrium. A needle cannula 54 carried on the distal end of the catheter is deployed to pierce the septum between the right and left atrium. As FIG. 21B shows, a guide wire 56 is advanced trans-septally through the needle catheter 52 into the left atrium. The first catheter 52 is withdrawn, and (as FIG. 21C shows) under image guidance, an implant delivery catheter 58 is advanced over the guide wire 56 into the left atrium into proximity with the mitral valve. Alternatively, the implant delivery catheter 58 can be deployed trans-septally by means of surgical access through the right atrium.

The distal end of the catheter 58 encloses an implant 400, like that shown in FIG. 8, which is constrained in a collapsed condition. A flexible push rod in the catheter 58 can be used to expel the implant 400 from the catheter 58. Free of the catheter, the implant 400 will self-expand to its preordained configuration, e.g., like that shown in FIG. 9A or 9B.

The implant 400 may be fixed to the annulus in various ways. For example, the implant 400 may be secured to the annulus with sutures or other attachment means (i.e. barbs, hooks, staples, etc.) Also, the implant 400 may be secured with struts or tabs 450 (see FIGS. 8 and 9A), that extend from the base 420 above or below the plane of the annulus. The struts 450 are preferably configured with narrow connecting members that extend through the valve orifice so that they will not interfere with the opening and closing of the valve.

In this arrangement, the struts 450 are desirably sized and configured to contact tissue near or within the heart valve annulus to brace the base 420 against migration within the annulus during the one-way valve function of the neoleaflet element. In this arrangement, it is also desirable that the base 420 be "elastic," i.e., the material of the base 420 is selected to possess a desired spring constant. This means that the base 420 is sized and configured to possess a normal, unloaded, shape or condition (shown in FIG. 8), in which the base 420 is not in net compression, and the struts 450 are spaced apart farther than the longest cross-annulus distance between the tissue that the struts 450 are intended to contact. In the illustrated embodiment, the base 420 is shown resting along the major (i.e., longest) axis of the valve annulus, with the struts 450 contacting tissue at or near the leaflet commissures. However, other orientations are possible. The struts 450 need not rest at or near the leaflet commissures, but may be significantly removed from the commissures, so as to gain padding from the leaflets. The spring constant imparts to the base 420 the ability to be elastically compressed out of its normal, unloaded condition, in response to external compression forces applied at the struts 450. The base 420 is sized and configured to assume an elastically loaded, in net compression condition, during which the struts 450 are spaced apart a sufficiently shorter distance to rest in engagement with tissue at or near the leaflet commissures (or wherever tissue contact with the struts 450 is intended to occur) (see FIG. 9A or 9B). When in its elastically loaded, net compressed condition (see FIGS. 9A and 9B), the base 450 can exert forces to the tissues through the struts 450. These forces hold the base 420 against migration within the annulus. Furthermore, when the struts 450 are positioned at or near the commissures, they tend to outwardly displace tissue and separate tissue along the major axis of the annulus, which also typically stretches the leaflet commissures, shortens the minor axis, and/or reshapes surrounding anatomic structures. The base 450 can also thereby reshape the valve annulus toward a shape more conducive to leaflet coaptation. It should be appreciated that, in order to be therapeutic, the implant may only need to reshape the annulus during a portion of the heart cycle, such as during ventricular systolic contraction. For example, the implant may be sized to produce small or negligible outward displacement of tissue during ventricular diastole when the tissue is relaxed, but restrict the inward movement of tissue during ventricular systolic contraction.

As the preceding disclosure demonstrates, different forms of heart valve treatment can be performed using a single implant.

Implants having one or more of the technical features just described, to thereby function in situ as a neo-leaflet, may be sized and configured in various ways. Various illustrative embodiments will now be described.

Figure 10:
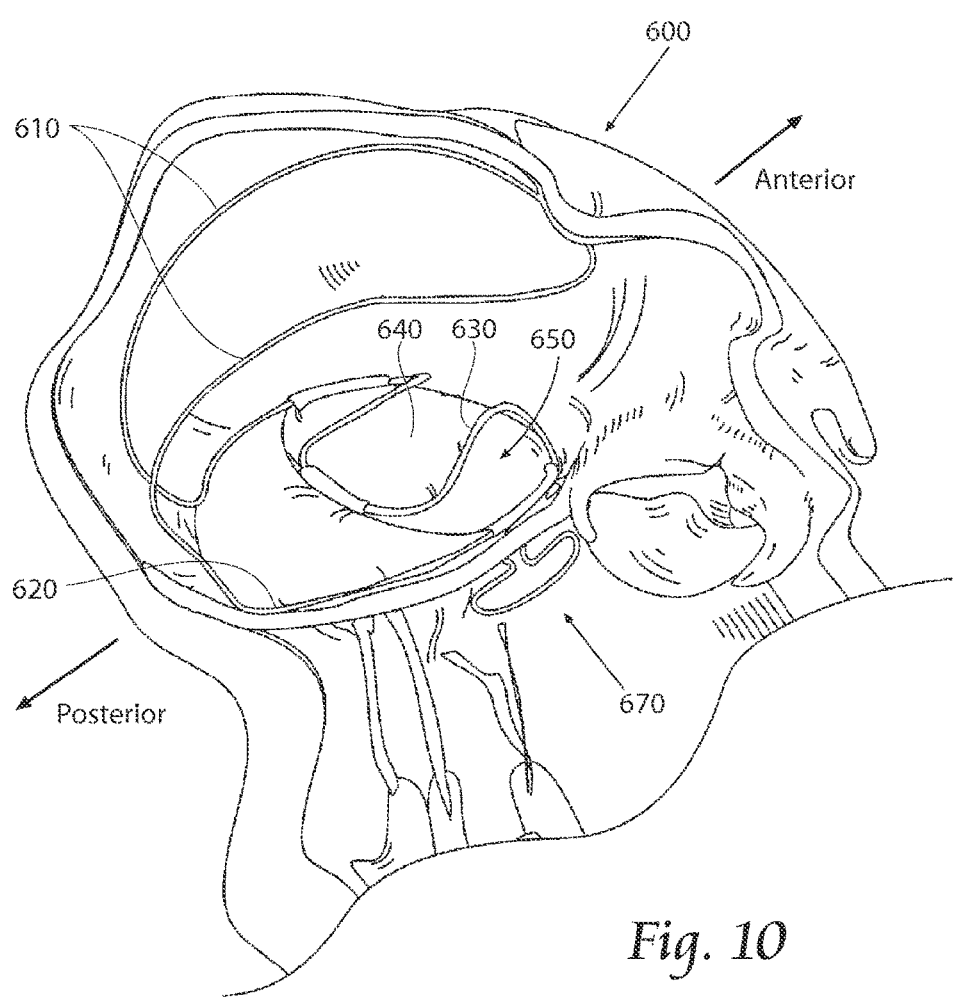
FIG. 10 is a perspective view of another illustrative embodiment of an implant that supplements, repairs, or replaces a native heart valve leaflet, the implant being shown installed on a mitral valve annulus and having a neoleaflet element that occupies the space of at least one native valve leaflet, the implant also including a framework that rises above the neoleaflet element in the atrium to help fix and stabilize the implant.

In FIG. 10, an implant 600 (like implant 400) includes a base 620 that defines a pseudo-annulus, with a bridge 630 carrying a spanning material 640 together comprising a neoleaflet element 650 appended to the base 620 within the pseudo-annulus. The neoleaflet element 650 overlays an anterior native leaflet with the same purpose and function described for the implant 400. Alternatively, the neoleaflet element 650 could overlay a posterior native leaflet, as FIG.

9B shows. The implant 600 also includes struts 670, which desirably contact and exert force against tissue near or within the annulus (in the manner previously described) to brace the base 420 against migration within the annulus.

In addition, the implant 600 includes an orientation and stabilization framework 610 that may extend from the annulus to the atrial dome. In FIG. 10, the framework 610 rises from the base 620 with two substantially parallel arched wires, which connect to form a semicircular hoop above the base 620. The framework 610 helps to accurately position the implant 600 within the atrium, and also helps to secure the implant 600 within the atrium.

Preferably the framework 610 does not interfere with atrial contractions, but instead is compliant enough to contract with the atrium. As such, the implant 600 may have nonuniform flexibility to improve its function within the heart.

Figure 11:
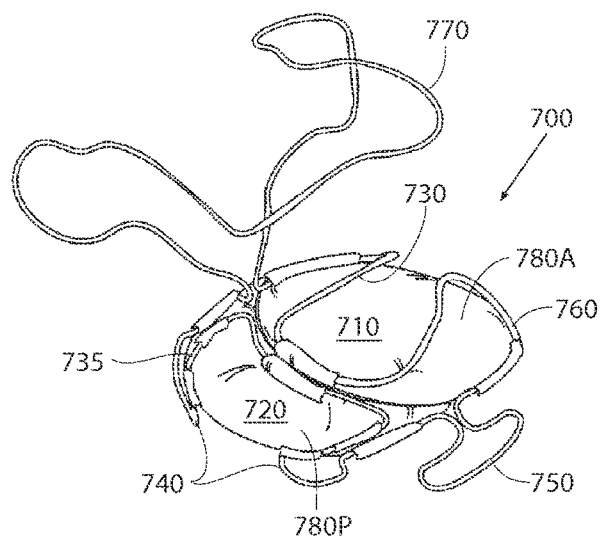
FIG. 11 is a perspective view of another illustrative embodiment of an implant that supplements, repairs, or replaces a native heart valve leaflet, the implant being sized and configured to extend about a heart valve annulus and including two neoleaflet elements that occupy the space of two native valve leaflets.

FIGS. 11 and 12 show another illustrative embodiment of an implant 700. In FIGS. 11 and 12, the implant 700 contains two neo-leaflet elements. The implant 700 includes an anterior bridge 730 spanned by an anterior bridge material 710, and a posterior bridge 735 spanned by a posterior bridge material 720. The bridges and materials together comprise anterior and posterior neoleaflet elements 780A and 780P. The implant 700 also includes an orientation and stabilization framework 770, shown having a configuration different than the framework 610 in FIG. 9, but having the same function and serving the same purpose as previously described for the framework 610.

In FIGS. 11 and 12, the base 760 includes structures like the anchoring clips 740 that, in use, protrude above the plane formed by the annulus of the valve. Additionally, the implant 700 may be secured with struts 750 that extend from the base 760 on narrow connecting members and below the plane of the annulus into the ventricular chamber. The anchoring clips 740 and struts 750 desirably contact and exert force against tissue near or within the annulus (in the manner previously described) to brace the base 760 against migration within the annulus. FIG. 11 shows the dual neo-leaflets 780A and 780B (i.e., the covered anterior and posterior bridges 730 and 735) in a closed valve position. FIG. 12 shows the dual neo-leaflets 780A and 780B in an open valve position.

Figure 13:
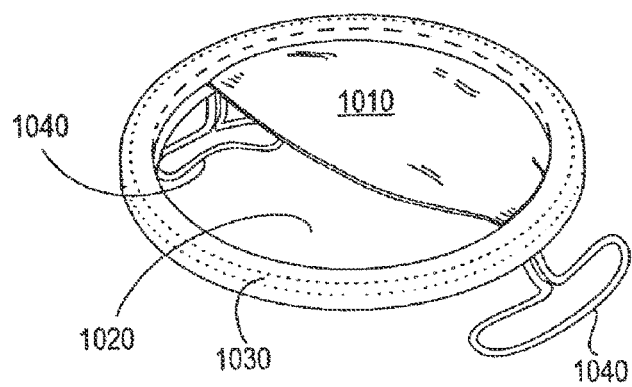
FIG. 13 is a perspective view of another illustrative embodiment of an implant that supplements, repairs, or replaces a native heart valve leaflet, the implant being sized and configured to extend about a heart valve annulus and including a neoleaflet element formed by a membrane.

FIG. 13 shows another illustrative embodiment of an implant 1000 having a full sewing ring 1030 with a membrane 1010 that serves as a neo-leaflet. The device 1000 has an opening 1020 though the sewing ring 1030 opposite the membrane 1010 for blood flow. Alternatively, this embodiment could have two neo-leaflets. This embodiment could be surgically attached to the valve annulus and/or combined with a framework for anchoring the device within the atrium using catheter based intraluminal techniques. Additionally, the device may be secured with struts 1040 that extend from the base on narrow connecting members and below the plane of the annulus into the ventricular chamber. The struts 1040, which desirably contact and exert force against tissue near or within the annulus (in the manner previously described) to brace the base 420 against migration within the annulus.

As can be seen, a given implant may carry various structures or mechanisms to enhance the anchorage and stabilization of the implant in the heart valve annulus. The mechanisms may be located below the plane of the annulus, to engage infra-annular heart tissue adjoining the annulus in the ventricle, and/or be located at or above the plane of the annulus, to engage tissue on the annulus or in the atrium. These mechanisms increase the surface area of contact between the implant and tissue. A given implant can also include tissue in-growth surfaces, to provide an environment that encourages the in-growth of neighboring tissue on the implant. Once in-growth occurs, the implant becomes resistant to migration or dislodgment from the annulus. Conventional in-growth materials such as polyester fabric can be used.

Figure 14:
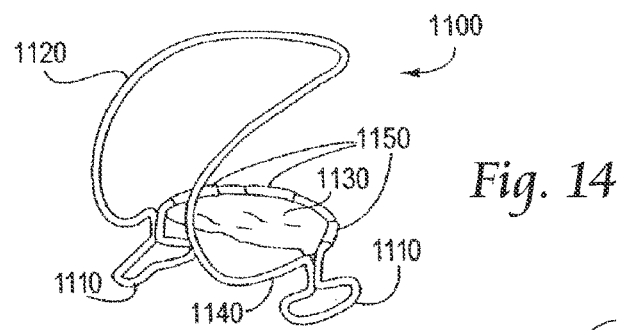
FIG. 14 is a perspective view of another illustrative embodiment of an implant that supplements, repairs, or replaces a native heart valve leaflet, the implant being sized and configured to extend about a heart valve annulus and including a neoleaflet element formed by a membrane, the implant also including a framework that rises above the neoleaflet element in the atrium to help fix and stabilize the implant.

FIG. 14 shows another illustrative embodiment of an implant 1100 having a framework 1120 and struts or tabs 1110. This implant 1100 includes a membrane 1130, that serves as a neo-leaflet, attached to the base 1140 of the device with an attachment means 1150.

Figure 15:
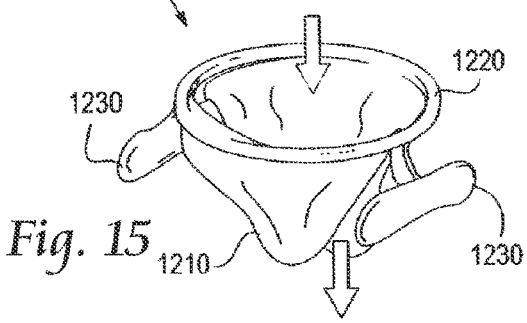
FIG. 15 is a perspective view of another illustrative embodiment of an implant that supplements, repairs, or replaces a native heart valve leaflet, the implant being sized and configured to extend about a heart valve annulus and including two neoleaflet elements to form a duckbill valve, the valve being shown in an opened condition as would exist during ventricular diastole.

FIG. 15 shows another illustrative embodiment of an implant 1200. In this embodiment, the implant 1200 includes a base 1220 that defines a pseudo-annulus and that, in use, is rests adjacent all or a portion of a native valve annulus. The base 1240 supports a duckbill valve 1210, which forms a neoleaflet element. Peripherally supported on the base 1240, the duckbill valve 1210 rests in the pseudo-annulus. Struts 1230 (which also carry additional tab structures to increase the surface area of tissue contact) help brace the base 1240 to tissue near or within the heart valve annulus.

Figure 16:
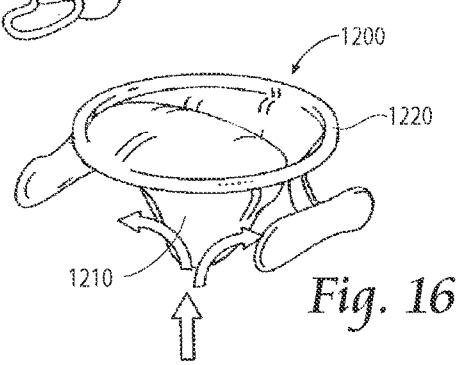
FIG. 16 is a perspective view of the implant shown in FIG. 15, the duckbill valve being shown in a closed condition as would exist during ventricular systole.

In this embodiment, the duckbill valve 1210 replaces the native anterior and posterior leaflets. The duckbill valve 1210 serves as dual neo-leaflets, which mutually open and close in response to changes in pressure, replacing the function of the native leaflets. FIG. 15 shows the duckbill valve 1210 in the open valve position. In FIG. 15, the arrow shows the direction of blood flow through the opened valve. FIG. 16 shows the duckbill valve in the closed valve position. When closed, the duckbill valve 1210 resists eversion and regurgitation.

Figure 17:
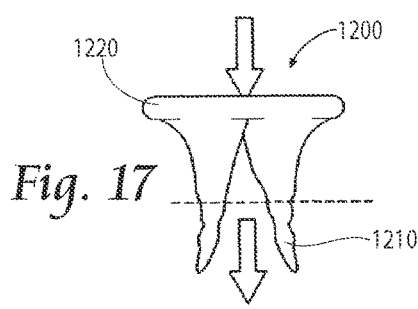
FIGS. 17 and 18 are side views of the implant shown, respectively, in FIGS. 15 and 16, with the duckbill valve, respectively, in an opened and a closed condition.
Figure 18:
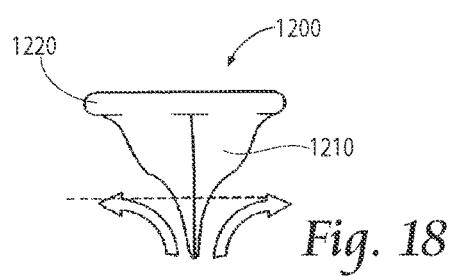

When the implant 1200 is used to replace a mitral valve (see FIGS. 17 and 18), the duckbill valve 1210 extends from the plane of the valve annulus and into the ventricle. The duckbill valve 1210 is shown to have a more rigid or thick composition emerging from the base member, and gradually becoming less rigid or thick away from the base member. This variation in mechanical properties ensures a valve that responds dynamically to pressure changes, but that is also rigid enough to not become everted. FIG. 17 shows the valve 1210 in an opened valve condition. In FIG. 17, the arrow shows the direction of blood flow through the opened valve. FIG. 18 shows the duckbill valve in the closed valve position, without eversion and regurgitation.

Figure 19:
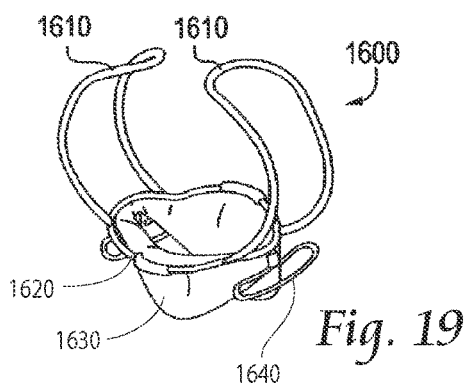
FIG. 19 is a perspective view of another illustrative embodiment of an implant that supplements, repairs, or replaces a native heart valve leaflet, the implant being sized and configured to extend about a heart valve annulus and including two neoleaflet elements formed by a duckbill valve, the valve being shown in an opened condition as would exist during ventricular diastole, the implant also including a framework that rises above the neoleaflet elements in the atrium to help fix and stabilize the implant.
Figure 20:
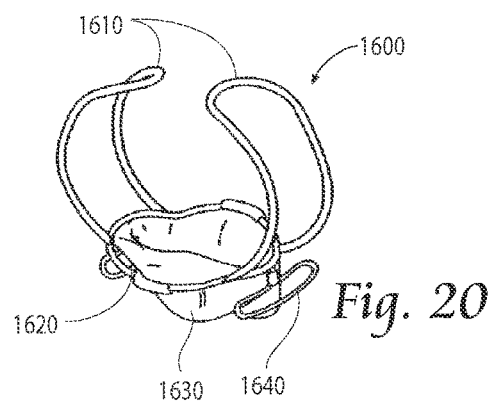
FIG. 20 is a perspective view of the implant shown in FIG. 19, the duckbill valve being shown in a closed condition as would exist during ventricular systole.

FIGS. 19 and 20 show another illustrative embodiment of an implant 1600 of the type shown in FIGS. 15 and 16. Like the implant 1200, the implant 1600 includes base 1620 defining a pseudo-annulus to which a duckbill valve 1630 is appended, which serves as a neoleaflet element to replace the native anterior and posterior leaflets and serves as dual neo-leaflets. FIG. 19 shows the duckbill valve 1630 in the open valve position, allowing forward flow of blood through the opened valve. FIG. 20 shows the duckbill valve 1630 in the closed valve position, resisting eversion and regurgitation.

In FIGS. 19 and 20, the implant 1600 includes an orientation and stabilization framework 1610. The framework 1610 rises from the base 1620 as two arches extending from opposite sides of the base 1620. The dual arch framework 1610 possesses compliance to contract with the atrium. As before explained, the framework 1610 helps to accurately position the implant 1600 within the atrium, and also helps to secure the implant 600 within the atrium. The implant 1600 also includes struts 1640, which desirably contact and exert force against tissue near or within the annulus (in the manner previously described) to brace the base 1620 against migration within the annulus.

While the new devices and methods have been more specifically described in the context of the treatment of a mitral heart valve, it should be understood that other heart valve types can be treated in the same or equivalent fashion. By way of example, and not by limitation, the present systems and methods could be used to prevent or resist retrograde flow in any heart valve annulus, including the tricuspid valve, the pulmonary valve, or the aortic valve. In addition, other embodiments and uses of the invention will be apparent to those skilled in the art from consideration of the specification and practice of the invention disclosed herein. The specification and examples should be considered exemplary and merely descriptive of key technical features and principles, and are not meant to be limiting. The true scope and spirit of the invention are defined by the following claims. As will be easily understood by those of ordinary skill in the art, variations and modifications of each of the disclosed embodiments can be easily made within the scope of this invention as defined by the following claims.

What is claimed is:

1. An implant for supplementing, repairing, or replacing a native heart valve having an annulus and a leaflet or leaflets comprising:
    a scaffold, at least a portion of the scaffold defining a pseudo-annulus, said pseudo-annulus having a circumference, the scaffold movable between an undeformed configuration and an elastically deformed condition by the application of external compressive force;
    the implant further comprising at least two struts, said struts in generally oppositely spaced apart positions along the circumference of the pseudo-annulus and depending downwardly below the plane of the pseudo-annulus, said struts biased away from each other when said scaffold is placed in said elastically deformed condition wherein when said scaffold is in said elastically deformed condition the struts may be placed in said valve with said pseudo-annulus adjacent said annulus to urge said annulus in an outward direction;
    the implant further comprising a neoleaflet element, said neoleaflet element comprising:
        a bridge supported by the scaffold, said bridge overlaying less than the full diameter of the pseudo-annulus when said scaffold is in said undeformed configuration; and
        a spanning material covering said bridge,
    said neoleaflet element being located within the pseudo-annulus when said scaffold is in said undeformed configuration in a manner that will, alone or in conjunction with the native leaflets, allow fluid to flow through the pseudo-annulus in one direction, but obstruct fluid flow in the opposite direction to provide, alone or in conjunction with one or more native leaflets, a one-way valve function within the annulus.

2. An implant for supplementing, repairing, or replacing the leaflets or leaflet of a native heart valve, the native heart valve having an annulus, the implant comprising:
    a scaffold, at least a portion of the scaffold defining a pseudo-annulus, the scaffold capable of moving from an elastically unloaded configuration to an elastically loaded configuration, in response to compression forces applied to said scaffold when said scaffold is in said elastically unloaded configuration, said scaffold is placed in said elastically loaded configuration has a spring constant which urges said scaffold toward said unloaded configuration, said scaffold defining a pseudo-annulus when in said unloaded configuration, said pseudo-annulus further having a circumference when in said unloaded configuration;
    said implant further comprising at least two struts coupled to the scaffold generally opposite one another along said circumference when the scaffold is in the unloaded configuration, said struts having a distance from one another when attached to said scaffold that is greater than the maximum cross-annulus distance,
    the implant further comprising a neoleaflet, said neoleaflet comprising:
        a bridge sized and configured to overlay the space of at least a portion of a native heart valve, and said bridge overlaying less than the full diameter of the pseudo-annulus when said scaffold is in said elastically unloaded configuration;
        and a spanning material covering said bridge;
    said neoleaflet coupled to the elastic scaffold within the pseudo-annulus and being sized and shaped to occupy the space of at least a portion of one native heart valve leaflet to provide, alone or in conjunction with the native heart valve leaflets, a one-way valve function,
    wherein, when the scaffold is placed in a chamber of the heart in the elastically unloaded condition and placed into the elastically loaded condition by application of compression forces to reduce the cross-strut distance, and simultaneously the struts are placed into engagement with tissue at or near the annulus, the implant will be held in place within the heart and will provide, alone or in conjunction with the native heart valves, a one-way valve function to the heart valve.

3. A heart valve structure for treating a human or animal heart having an annulus and leaflet commissures, the structure comprising
    a scaffold defining a pseudo-annulus, the scaffold having an elastically loaded configuration and including struts for engaging tissue at or near the valve leaflet commissures to reshape the annulus for leaflet coaptation, said struts having a dependent leg attached to said pseudo-annulus and a longitudinal section, said longitudinal section at a spaced apart distance from said pseudo-annulus, the scaffold also including a single neoleaflet element within the pseudo-annulus to provide, alone or in conjunction with the native heart valves, a one-way valve function; and
    said neoleaflet element further comprising
        a bridge supported by the scaffold, said bridge sized and configured to overlay the space of at least a portion of a native heart valve, said bridge extending less than the full diameter of said pseudo-annulus; and
        a spanning material covering said bridge.

* * * * *